(12) United States Patent
West, Jr. et al.

(10) Patent No.: US 6,618,626 B2
(45) Date of Patent: Sep. 9, 2003

(54) APPARATUS AND METHODS FOR PROTECTING THE AXILLARY NERVE DURING THERMAL CAPSULLORHAPHY

(75) Inventors: Hugh S. West, Jr., Salt Lake City, UT (US); John S. Gentelia, Madison, NY (US)

(73) Assignee: HS West Investments, LLC, Salt Lake City, UT (US)

( * ) Notice: Subject to any disclaimer, the term of this patent is extended or adjusted under 35 U.S.C. 154(b) by 0 days.

(21) Appl. No.: 09/942,169

(22) Filed: Aug. 29, 2001

(65) Prior Publication Data

US 2002/0095199 A1 Jul. 18, 2002

Related U.S. Application Data

(60) Provisional application No. 60/261,388, filed on Jan. 16, 2001.

(51) Int. Cl.[7] ............................................. A61F 2/00
(52) U.S. Cl. ........................................ 607/101; 606/34
(58) Field of Search ........................ 606/41, 46, 49, 606/37; 607/96, 99, 101, 102

(56) References Cited

U.S. PATENT DOCUMENTS 5,409,485 A * 4/1995 Suda ............................ 606/34
6,139,545 A * 10/2000 Utley et al. ................... 606/34
6,405,732 B1 * 6/2002 Edwards et al. ............ 128/898

* cited by examiner

Primary Examiner—Roy D. Gibson
Assistant Examiner—Aaron Roane
(74) Attorney, Agent, or Firm—Workman Nydegger (57) ABSTRACT

This invention provides apparatus and means for protecting the axillary nerve during thermal capsullorhaphy. An electrosurgical probe is attached to a standard electrosurgical generator that is capable of producing coag waveforms. RF energy is generated by the generator in coag waveform and applied to discrete locations of the capsular ligaments through the electrosurgical probe. Noise produced by the coag waveform stimulates the axillary nerve, even in saline environments, thereby identifying the high-risk regions of the capsular ligaments that should be avoided during the procedure.

25 Claims, 4 Drawing Sheets

APPARATUS AND METHODS FOR PROTECTING THE AXILLARY NERVE DURING THERMAL CAPSULLORHAPHY

RELATED APPLICATIONS

This application claims the benefit under 35 U.S.C. □119 of U.S. Provisional Patent Application Ser. No. 60/261,388 entitled "Axillary Nerve Stimulation," filed Jan. 16, 2001, which is incorporated herein by reference.

BACKGROUND OF THE INVENTION

1. The Field of the Invention

The present invention relates to the field of electrosurgical probes and procedures for performing endoscopic thermal capsullorhaphy. In particular, the invention relates to electrosurgical probes and methods for locating and protecting the axillary nerve while performing arthroscopic thermal capsullorhaphy on the human shoulder.

2. The Prior State of the Art

The joint of the human shoulder provides the greatest range of motion of all the joints in the human body. However, when ligaments of the shoulder become stretched or damaged the shoulder can suffer from a condition known as shoulder instability, which can significantly limit the function of the shoulder. Shoulder instability can result from a violent injury that causes the shoulder to dislocate, or by a repetitive injury that stretches the ligaments of the shoulder over a period of time. Shoulder instability, if not cured, may cause chronic pain, arthritis, and loss of function.

Shoulder instability can sometimes be treated with rehabilitation. However, if rehabilitation is not successful or appropriate then surgery may be required. Surgery generally involves the tightening of lax and over-stretched capsular ligaments. Some surgical techniques, referred to as "capsular shift procedures," tighten and generally reconstruct the capsular ligaments of the shoulder.

Capsular shift procedures can be performed by open surgery or by arthroscopic surgery. Open surgery often results in greater post-operative pain and requires more extensive rehabilitation than arthroscopic surgery. Accordingly, as arthroscopic techniques continue to develop, they are increasingly chosen as the preferred method in the treatment of shoulder instability.

One recent advance in arthroscopic surgery, which is known as thermal capsullorhaphy, offers distinct advantages over capsular shift procedures and other similar techniques because it does not require the surgical reconstruction of the ligament capsules. This technique, which is also known as "thermal capsulorraphy," "thermal capsular shrinking," "radiofrequency thermal shrinking," and "thermal capsular shift," involves the non-contact shrinking of the capsular ligaments by heating the collagen fibers within the capsular ligaments with a radiofrequency probe (electrode) operating in either a bipolar or monopolar mode.

One problem associated with thermal capsullorhaphy, however, is that the temperature required to shrink the capsular ligaments can cause severe nerve damage. In particular, nerves have been shown to sustain irreversible injury at temperatures exceeding 55° C., yet the minimum temperature required to shrink collagen and the capsular ligaments is known to be approximately 65° C., with actual procedural temperatures approaching 100° C.

Of particular interest is the axillary nerve, also known as the circumflex nerve, which passes directly beneath the inferior gleno-humeral capsular ligament of the shoulder, placing it at risk for thermal injury during thermal capsullorhaphy. Temporary injury to the axillary nerve, also known as axillary neuropraxia, as well as permanent thermal injury to the axillary nerve, are possible consequences of thermal capsullorhaphy because the intraarticular anatomic landmarks defining the course of the axillary nerve are vague, thereby making it difficult to identify and to avoid applying heat to the regions of tissue where the nerve is proximate the capsular ligaments. Although the temperatures that are applied to the capsular ligaments during thermal capsullorhaphy decrease exponentially with tissue depth, temperatures in excess of 55° C. can easily be achieved at the minimal depths where the axillary nerve is located proximately to the capsular ligaments. Compounding this problem is the fact that the measured distance between the axillary nerve and the capsule ligaments in cadaveric specimens varies widely, suggesting that thermal capsullorhaphy creates a greater risk of axillary nerve injury for certain shoulders than for others.

Axillary neuropraxia and permanent damage to the axillary nerve can be avoided by using nerve stimulating devices to stimulate the axillary nerve and to identify the high-risk regions where the axillary nerve is extremely close to the capsular ligaments. The high-risk regions can then be avoided so that the axillary nerve is not overheated during the procedure. Existing nerve stimulating devices, typically used to identify nerves to be anesthetized, emit direct current ("DC") pulses that stimulate motor nerves such as the axillary nerve. When a motor nerve is stimulated, it causes the muscles supplied by the nerve to contract. The visual observation of stimulating the axillary nerve, for example, is a physical jump or movement of the deltoid muscle.

Existing nerve stimulating devices, however, are not suitable for arthroscopic procedures. Arthroscopic procedures require the surgical site to be filled with a saline solution, which is highly conductive and which diffuses the DC energy before it can stimulate the axillary nerve, thereby making it difficult to identify and locate the high-risk regions of the capsular ligament that should be avoided during thermal capsullorhaphy.

Some existing RF electrodes are configured with temperature sensors located in the tip of the electrode for controlling the temperatures that are generated by the electrode. The temperature sensor in effect measures existing local surface temperatures and controls the RF energy that is applied by the electrode to the capsular ligaments. The benefit of temperature sensor electrodes in protecting the axillary nerve, however, is extremely limited. In particular, these electrodes are unable to identify the high-risk regions where the axillary nerve passes the capsular ligaments.

Accordingly, there is presently a need in the art for improved methods and devices that are able to locate the high-risk regions of the capsular ligaments during arthroscopic thermal capsullorhaphy in order to reduce the risk of axillary neuropraxia.

SUMMARY OF THE INVENTION

The present invention is directed to improved apparatus and methods for protecting the axillary nerve during thermal capsullorhaphy. In particular, the present invention is directed to systems comprising improved radiofrequency (RF) electrosurgical devices and methods for identifying and avoiding regions of the capsular ligaments that are in extremely close proximity to the axillary nerve, thereby reducing the risk of axillary neuropraxia or permanent damage to the axillary nerve while performing arthroscopic thermal capsullorhaphy. The apparatus and methods of the invention utilize what is known in the art as a coagulation or "coag" RF waveform to stimulate and locate the axillary nerve preparatory to, or during, thermal capsullorhaphy.

The systems of the invention utilize intraoperative electrical stimulation of the axillary nerve as the means of identifying the anatomically "high-risk" regions of the capsular ligaments that should be avoided during the thermal capsullorhaphy procedure. By avoiding the high-risk regions it is possible to minimize the likelihood of causing thermal damage to the axillary nerve.

According to one embodiment, an RF electrosurgical probe is electrically connected to a standard electrosurgical generator that is capable of producing RF energy having a coag waveform. The electrosurgical probe is equipped with a tip for dispensing the RF energy and a power cord that supplies RF energy from the generator. The probe may optionally include different activation switches depending on whether one wishes to shrink ligament tissue or perform nerve stimulation.

The electrosurgical probe can operate in a nerve stimulation mode and a tissue shrinkage mode. In the nerve stimulation mode, a quantity of RF energy is emitted from the electrosurgical probe that at least indirectly causes a nerve within a nerve stimulation zone to be stimulated, but which is insufficient to cause thermal damage to the nerve. The nerve stimulation zone is the area directly around the tip of the probe that receives a sufficiently strong stimulation signal to stimulate a nerve In the tissue shrinkage mode, RF energy is continuously emitted from the tip of the electrosurgical probe so as to thermally shrink tissue in a tissue shrinkage zone surrounding the tip of the electrosurgical probe. The tissue shrinkage zone is essentially the area surrounding the tip of the electrosurgical probe that receives sufficient RF energy to cause tissue to thermally shrink.

In one embodiment, a stimulation signal comprises electrical noise that is a byproduct of RF energy having a coag waveform. The present invention enables a surgeon to identify high-risk regions where the axillary nerve passes in close proximity to the inferior gleno-humeral ligament by applying the stimulation signal to a treatment region where shoulder tissue is intended to be shrunk. The stimulation signal is applied in short bursts to stimulate the axillary nerve and to identify the high-risk regions of the capsular ligament, usually limited in size to about one square centimeter, that are located within such close proximity to the axillary nerve that thermally shrinking at those regions would likely cause thermal damage to the axillary nerve. Stimulating a nerve, such as the axillary nerve, can be accomplished according to the invention, even in a saline environment, such as during endoscopic surgery.

In one preferred embodiment, the stimulation signal is applied by the electrosurgical probe, in a nerve stimulation mode, at discrete location points over the entire area of treatment region where shoulder tissue is intended to be shrunk, thereby identifying any high-risk regions that should be avoided during thermal capsullorhaphy. Once the entire treatment region has been prospected for high-risk regions, the electrosurgical probe is used to emit high frequency energy having a coag or a cut waveform to heat and contract the collagen fibers of the tissue within the treatment region. Any high-risk regions are avoided during this step, thereby protecting the axillary nerve from thermal damage.

According to another embodiment, the stimulation signal is applied by the electrosurgical probe, in a nerve stimulation mode, to shoulder tissue at a small region and if the axillary nerve is not stimulated at that region then RF energy is applied by the electrosurgical probe, in a tissue shrinkage mode, to the shoulder tissue within that region until the shoulder tissue is heated to a sufficient temperature to cause thermal shrinking. The tip of the electrosurgical probe is then move to a new small region and the process is repeated. If the axillary nerve is stimulated at a given region, then the shoulder tissue at that region is passed over and not directly heated with RF energy.

It should be appreciated that the present invention generally enables a surgeon to prospect for a nerve, such as the axillary nerve, using an RF electrode employing a coag waveform that is generated from a standard electrosurgical generator. In so doing, the invention generally minimizes the risk of axillary nerve injury during thermal capsullorhaphy.

These and other features and advantages of the present invention will become more fully apparent from the following description and appended claims, or may be learned by practicing the invention as set forth below.

BRIEF DESCRIPTION OF THE DRAWINGS

A more extensive description of the present invention, including the above-recited features and advantages, will be rendered with reference to the specific embodiments that are illustrated in the appended drawings. Because these drawings depict only exemplary embodiments, the drawings should not be construed as imposing any limitation on the present invention's scope. As such, the present invention will be described and explained with additional specificity and detail through use of the accompanying drawings in which:

FIG. 4 is a top view of a treatment region of shoulder tissue of the inferior gleno-humeral ligament that shows location points where the stimulation signal is applied and a high-risk region which is identified while applying the stimulation signal according to the invention. FIG. 4 also shows a phantom image of the axillary nerve where it passes in proximity to the inferior gleno-humeral ligament;

DETAILED DESCRIPTION OF THE PREFERRED EMBODIMENTS

The present invention relates to methods and systems for identifying regions of the capsular ligaments that are within such close proximity to the axillary nerve that they should be avoided while performing thermal capsullorhaphy in order to minimize the likelihood of causing injury to the axillary nerve during the procedure.

According to one present embodiment of the invention, the axillary nerve is protected while performing thermal capsullorhaphy on the gleno-humeral capsular ligaments of the human shoulder to treat shoulder instability. Thermal capsullorhaphy generally involves thermal shrinking of collagen fibers of the capsular ligaments with radiofrequency (RF) energy, thereby reducing the volume of the capsular ligaments and generally tightening the capsular ligaments about the shoulder.

One risk associated with thermal capsullorhaphy is axillary neuropraxia, or damage to the axillary nerve, which can occur when the axillary nerve is heated above 55° C. This is possible during thermal capsullorhaphy because the tissue of the capsular ligaments have to be heated to at least 65° C., and in practice are often heated up to 100° C., before the collagen fibers are caused to shrink. Because the axillary nerve is located in close proximity to the inferior gleno-humeral capsular ligament, it is possible for the axillary nerve to be critically heated over 55° C. when the tissue of the inferior gleno-humeral ligament, which is proximate the axillary nerve, is heated to 65° C.

To minimize the likelihood of overheating the axillary nerve, the present invention provides apparatus and methods for identifying the high-risk regions of the capsular ligaments that are within close proximity to the axillary nerve so that they can be avoided during thermal capsullorhaphy, thereby minimizing the likelihood of causing thermal damage to the axillary nerve during the procedure.

Figure 1:
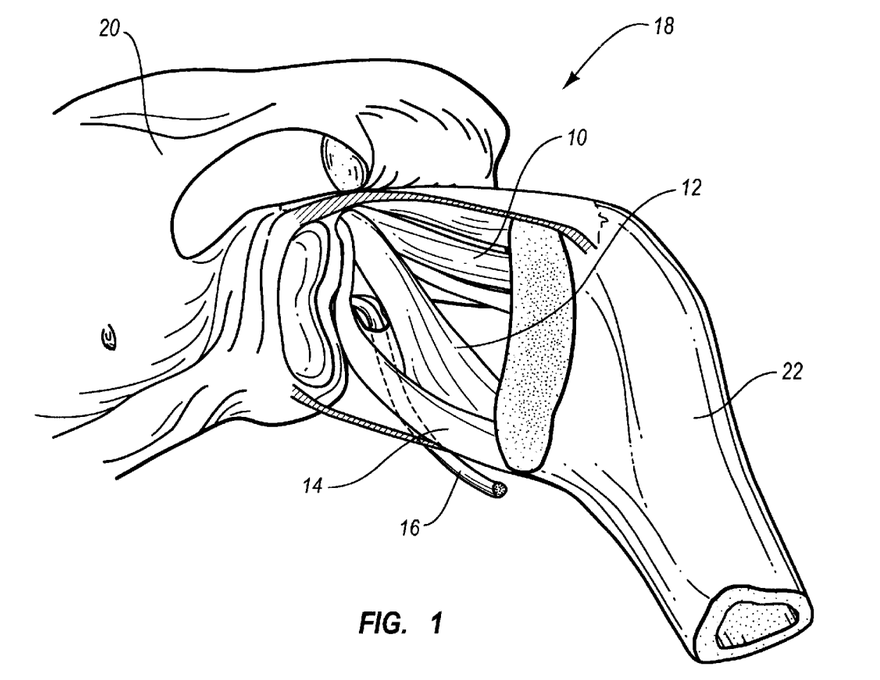
FIG. 1 is a partial cross-sectional view of the human shoulder that generally shows the anatomical location of the axillary nerve with respect to the superior, middle, and inferior gleno-humeral ligaments.

FIG. 1 illustrates the general anatomy of the gleno-humeral ligaments of the human shoulder and their relative locations with respect to the axillary nerve. As shown, there are three gleno-humeral ligaments, namely, the superior gleno-humeral ligament 10, the middle gleno-humeral ligament 12, and the inferior gleno-humeral ligament 14. The inferior gleno-humeral ligament 14, which is of particular interest in the present application, is also referred to herein as the "inferior ligament," "inferior capsular ligament," "capsular ligament," and "ligament."

The three gleno-humeral ligaments 10, 12, and 14 generally provide the shoulder joint 18 with stability. As shown, the shoulder joint 18 includes the scapula 20 and the humerus 22. When the ligaments 10, 12, and 14 become stretched or otherwise too lax, then the shoulder joint becomes unstable. Shoulder instability may be treated, as noted above, by performing thermal capsullorhaphy on the lax shoulder tissues of the capsular ligaments. However, also as noted above, this procedure is associated with a risk for causing thermal damage to the axillary nerve (axillary neuropraxia).

As shown in FIG. 1, the axillary nerve 16 runs directly beneath the inferior ligament 14, but only makes limited contact with the inferior ligament 14 before it branches off to supply the deltoid muscles of the shoulder (not shown). Nevertheless, because the axillary nerve 16 is located in such close proximity to the inferior ligament 14, it is at risk of being thermally damaged when the inferior ligament 14 is heated to 65° C., as required for thermal capsullorhaphy. In particular, the heat that is generated at the inferior ligament 14 can transfer to the axillary nerve 16 and heat the axillary nerve 16 to a temperature over 55° C., which will cause nerve damage.

Accordingly, to minimize the potential risk to the axillary nerve 16 during thermal capsullorhaphy, it is desirable to avoid the "high-risk" regions of the capsular ligament 14. The term "high-risk region" is generally defined herein to include the region of tissue that is located within such close proximity to the axillary nerve or another nerve that performing thermal capsullorhaphy at that region will cause thermal damage to the nerve.

The present invention overcomes problems of the prior art by providing systems for stimulating the axillary nerve and for identifying the high-risk regions of the capsular ligament that should be avoided during thermal capsullorhaphy, thereby protecting the axillary nerve during the procedure. The systems of the present invention include an electrosurgical probe, an electrosurgical generator, and a method for using the electrosurgical probe and generator to protect the axillary nerve during thermal capsullorhaphy.

Figure 2:
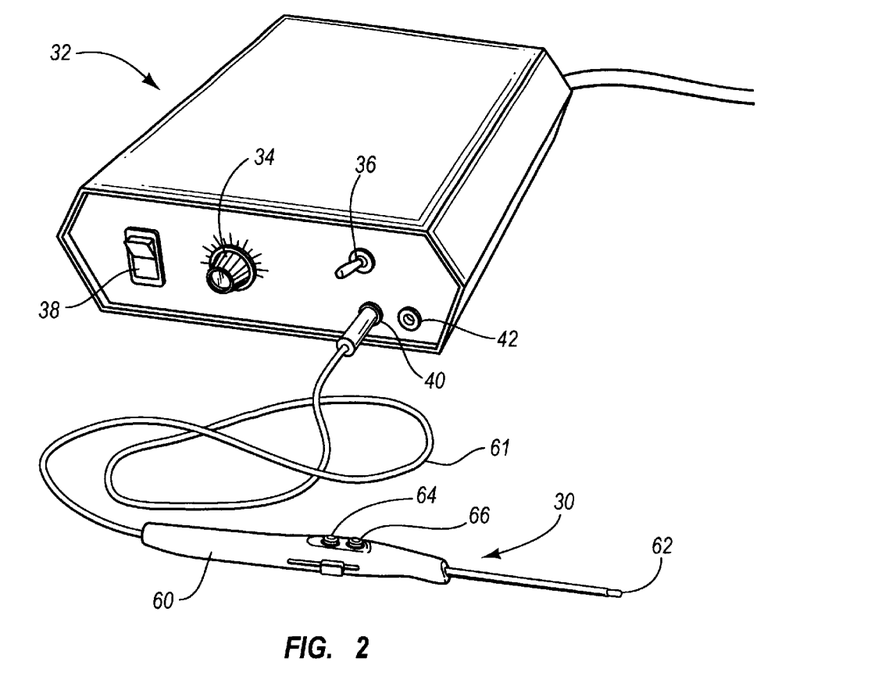
FIG. 2 shows one embodiment of a standard radiofrequency generator and one embodiment of the radiofrequency electrosurgical probe of the invention.

FIG. 2 illustrates one embodiment of the electrosurgical probe 30 of the invention which is attached to a standard electrosurgical generator 32. The electrosurgical generator 32 is considered "standard" because it is configured to perform standard surgical functions, namely, to generate RF energy having cut and coag waveforms. However, it should be appreciated that electrosurgical generator 32 can be one of any standard or non-standard electrosurgical generators that currently exist or that may be developed in the future, and which are configured for generating RF energy in both cut and coag waveforms.

In one embodiment, electrosurgical generator 32 comprises standard components, such as a dial 34 for controlling the frequency and/or amplitude of the RF energy, a switch 36 for changing the type of waveform generated (e.g., between "cut" and "coag" waveforms), a switch 38 for turning the generator on and off, a power receptacle 40 for connecting to the radiofrequency probe 30, and an electrical ground receptacle 42 for connecting to a conductive ground plate during monopolar thermal capsullorhaphy, which is described below in more detail.

It will be appreciated that electrosurgical generator 32, of FIG. 2, is merely suggestive of one suitable electrosurgical generator for use in practicing the present invention and in no way limits the scope of the invention. The electrosurgical generator may, for example, as a matter of illustration and not limitation, further comprise other components, such as a display for indicating the frequency, amplitude and/or type of waveform that is generated by the electrosurgical generator.

According to one preferred embodiment, the electrosurgical generator 32 supplies the electrosurgical probe with RF energy having cut and coag waveforms. According to an alternative embodiment, electrosurgical generator 32 is configured to supply RF energy having only coag waveforms. In yet another embodiment, the systems of the invention may comprise two separate RF generators, a first generator that only produces coag waveforms, and a second generator that produces only cut waveforms, each of which are supplied to the electrosurgical probe of the invention.

Cut and coag waveforms can be used to heat tissue and are well known in the art of surgical procedures. Cut waveforms are generally used for "cutting" or ablating tissue, while coag waveforms are generally used for "coagulation" or desiccation; hence, the terms cut and coag.

Figure 3:
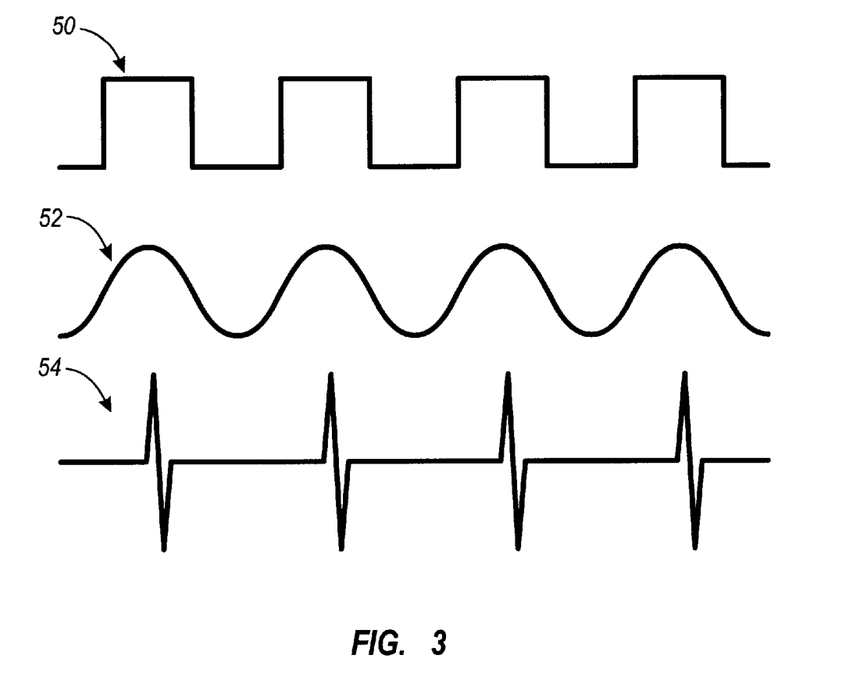
FIG. 3 shows three different waveforms, including a rectangular cut waveform, a sinusoidal cut waveform, and a coag waveform.

FIG. 3 shows three different waveforms, including rectangular cut waveform 50, sinusoidal cut waveform 52, and coag waveform 54. Each of these waveforms is suitable for transmitting high frequency alternating current (AC) RF energy to the capsular ligaments during thermal capsullorhaphy. The RF energy creates heat and shrinks the capsular ligaments when the ligament tissue is heated in the general range of 65° C. to 100° C. Typically, RF energy is applied at a frequency of about 450 KHz, but it may vary. The frequency must, however, be high enough so as to avoid the unnecessary risk of electrical shock and electrocution. According to one embodiment, the frequency of RF energy is applied within a preferred range of approximately 100 KHz to approximately 500 KHz.

According to the preferred embodiment, the electrosurgical generator also supplies the electrosurgical probe with a stimulation signal, which is capable of stimulating the axillary nerve, even in a saline environment, such as during endoscopic surgery.

In one embodiment, the stimulation signal comprises electrical "noise" that is a harmonic byproduct of RF energy having a coag waveform. As shown in FIG. 3, the coag waveform 54 consists of periodic, high amplitude pulses (larger than the cut waveform 50 and 52) that are spaced by long quiescent time periods. This produces electrical noise that is sufficient to stimulate motor nerves, such as the axillary nerve, even in a saline environment. This is in contrast to the cut waveforms 50 and 52, which will rarely stimulate a nerve.

The visual observation of stimulating the axillary nerve is a physical movement or jump of the deltoid muscle. When viewed arthroscopically, the effect is a jump or movement in the field of view of the arthroscope. Electrical stimulation of the axillary nerve is a benign procedure and short bursts of RF energy at low power using a coag waveform have no capacity to create a thermal injury to the axillary nerve.

The stimulation signal is dispensed from the electrosurgical probe 30 of FIG. 2. According to one preferred embodiment, the electrosurgical probe 30 comprises a body 60, a cord 61, and a tip 62. The shape and design of the body 60 is not critical and may vary to accommodate manufacturing efficiency and ergonomics. The cord 61 is one means for connecting the electrosurgical probe 30 to the electrosurgical generator 32. According to one embodiment, the cord 61 is integrally connected to the electrosurgical probe 30 and can be removably coupled within the power receptacle 40 of the electrosurgical generator 32.

The tip is small and narrow, being configured in shape and size for endoscopic surgery. It should be appreciated, however, that the tip 62 is not limited to any particular shape, size, or location on the electrosurgical probe 30. Accordingly, the "tip" 62 should be broadly construed to include any portion of the electrosurgical probe 30 where RF energy is emitted from an electrode.

The tip 62 may comprise at least one of two general embodiments for accommodating two basic modes of electrosurgery, namely, the bipolar mode and the monopolar mode. For electrosurgery in the bipolar mode, the tip 62 comprises two electrodes (not shown), including an active electrode and a return electrode, such that the RF energy is dispersed between the two electrodes. In the monopolar mode, the tip 62 only comprises an active electrode, with the RF energy being dispersed between the active electrode and a ground plate (not shown) that is attached to the patient and connected to the electrical ground receptacle 42. It should be appreciated that the electrosurgical probe 30 of the invention can be configured with any tip that is suitable for performing thermal capsullorhaphy in either of the bipolar and monopolar modes of electrosurgery.

As shown, the electrosurgical probe 30 of the invention may also comprise a switch 64 for controlling the application of RF energy in either cut or coag waveform during surgery, in a tissue shrinkage mode. The electrosurgical probe may also comprise a switch 66 for controlling the application of the stimulation signal during surgery, in a nerve stimulation mode. Switches 64 and 66 are disposed within body 60 and effectively act as "on" and "off" controls for determining when the RF energy and stimulation signal are emitted from the tip 62. For example, according to one embodiment, switches 64 and 66 are "on" when they are depressed, and they are "off" when they are released.

According to one presently preferred embodiment, when switch 66 is in the "on" position it causes the electrosurgical probe 30 to operate in a nerve stimulation mode in which it emits a short burst, or repeating short bursts, of the stimulation signal. The bursts are preferably emitted for time durations less than about 0.5 second, more preferably less than about 0.1 second, although any time duration that avoids thermal damage to the nerve would be within the scope of the invention. The short bursts are sufficient to stimulate the axillary nerve within the nerve stimulation zone without causing thermal damage to the nerve within the nerve stimulation zone. According to one preferred embodiment, the stimulation signal comprises noise that is a byproduct of RF energy having a coag waveform. According to this embodiment, the electrosurgical probe emits short bursts of RF energy having a coag waveform when it is in the nerve stimulation mode. When the electrosurgical probe is caused to operate in the tissue shrinkage mode then the electrosurgical probe continuously emits RF energy in either coag or cut waveform that is sufficient to cause tissue to thermally shrink. The electrosurgical probe emits RF energy in a tissue shrinkage zone that surrounds the tip of the electrosurgical probe, such that any collagen tissue within the tissue shrinkage zone will be heated from the RF energy and caused to shrink.

The electrosurgical probe of the invention may also comprise means for identifying when the electrosurgical probe is operating in the nerve stimulation mode, in the tissue shrinkage mode, or simultaneously in both the nerve stimulation and tissue shrinkage modes. Means for identifying what mode the electrosurgical probe is operating in may comprise labels. For instance, labels can be affixed next to buttons 64 and 66 for identifying the functions of the buttons 64 and 66 and for indicating what mode the electrosurgical probe will be in when the buttons are pressed. As a matter of example and not limitation, a first label affixed near or on button 66 may display the words "stimulate" and a label affixed near or on button 64 may display the words "shrink."

Means for identifying what mode the electrosurgical probe is operating in may also comprise an illuminated display that can be affixed to the electrosurgical probe 30 and/or affixed to the electrosurgical generator 32. The illuminated display(s) can indicate the mode of operation of the electrosurgical probe by illuminating symbols, colors, letters, numbers, or any combination thereof, such as when buttons 64 and 66 are pressed.

Methods for using the electrosurgical probe and electrosurgical generator for protecting the axillary nerve during thermal capsullorhaphy will now be discussed in reference to FIGS. 4–6.

Figure 4:
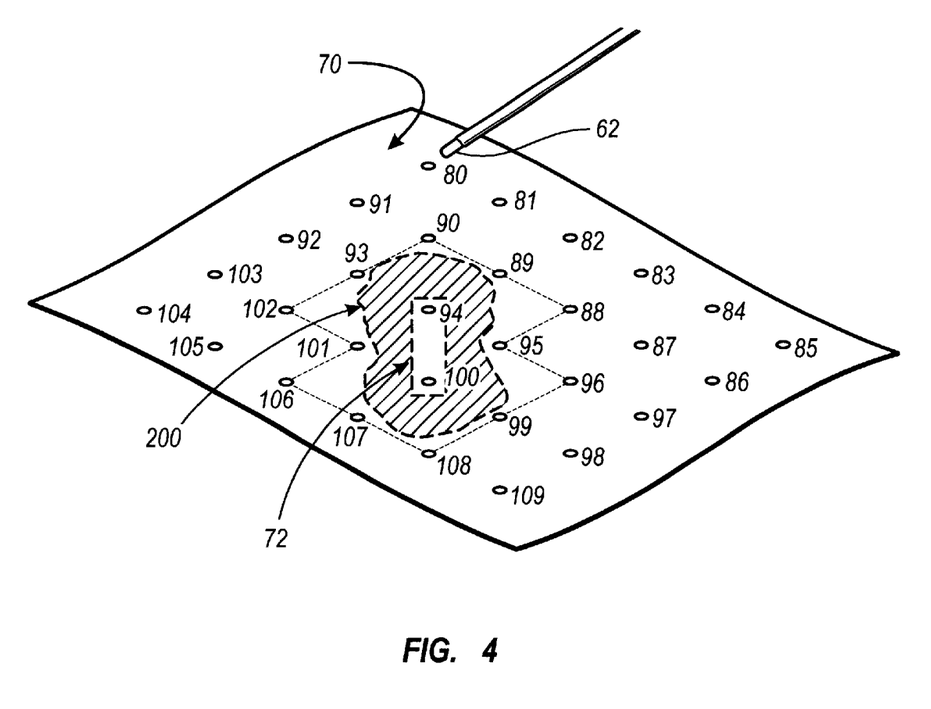

FIG. 4 illustrates a top view of a treatment region 70 of shoulder tissue intended to be thermally shrunk. A phantom image of the axillary nerve 72 is also illustrated to show where, according to the current embodiment, the axillary nerve passes within close proximity to the treatment region 70. FIG. 4 also illustrates several location points 80–109 that are suitable locations for applying the stimulation signal to the treatment region 70 while prospecting for high-risk regions that should be avoided while performing thermal capsullorhaphy. It should be appreciated, however, that other locations may also be appropriate.

Figure 5:
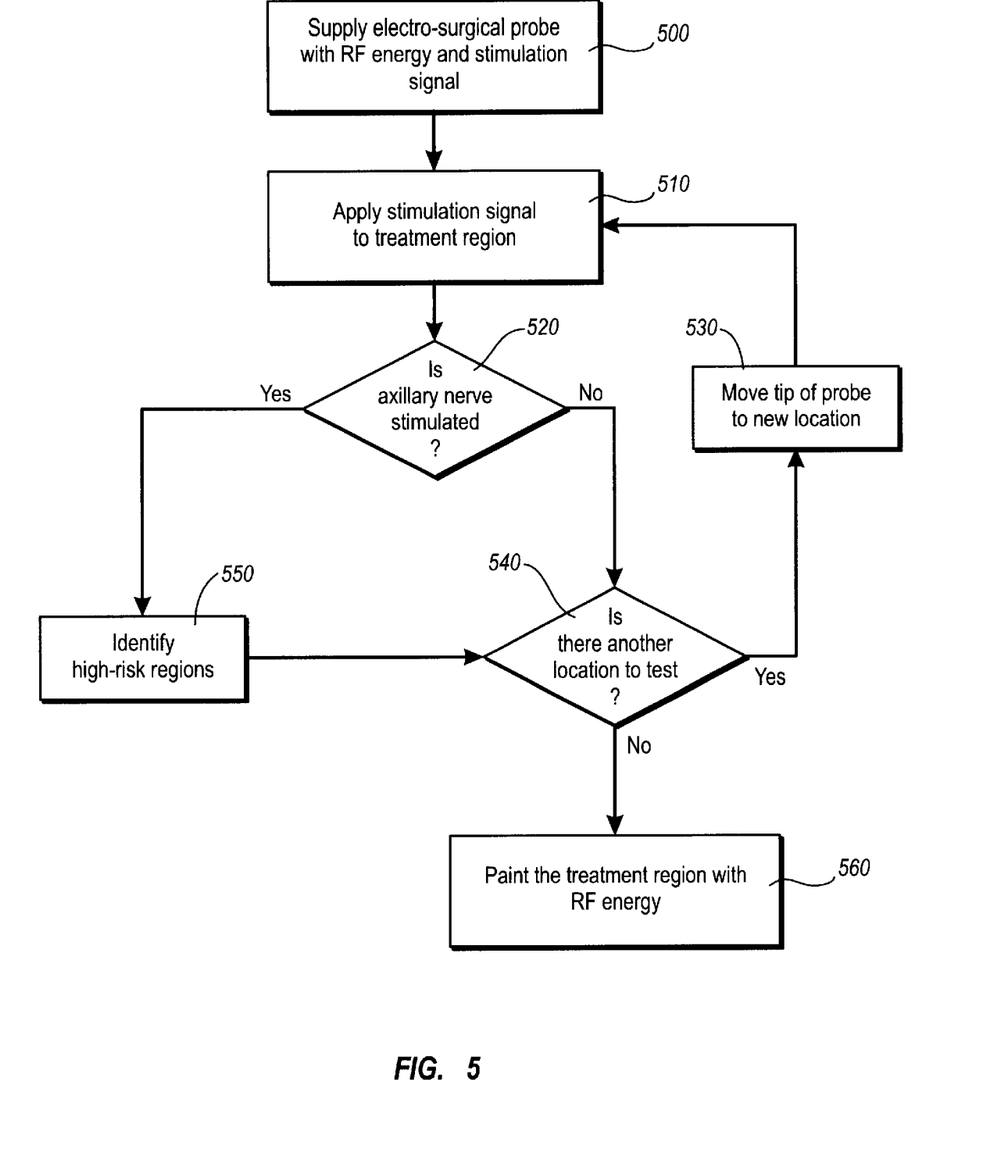
FIG. 5 is a flow diagram that illustrates one embodiment of the methods of the present invention for protecting the axillary nerve while performing thermal capsullorhaphy.

According to one embodiment, a method for protecting the axillary nerve from thermal injury during thermal capsullorhaphy according to the invention comprises the performance of various steps, which are generally illustrated in the flowchart of FIG. 5, and which will be described in general reference to FIG. 4.

The first step of the method of the present embodiment is to supply the electrosurgical probe with RF energy that is capable of thermally shrinking the shoulder tissue and with a stimulation signal that is capable of stimulating the axillary nerve, step 500. As described above, the RF energy may be embodied in either a cut or coag waveform. The stimulation signal may comprise electrical noise of RF energy having a coag waveform. The stimulation signal and the RF energy are supplied to the electrosurgical probe by the electrosurgical generator, as described above in reference to FIG. 2.

Next, in step 510, the stimulation signal is applied to the treatment region where shoulder tissue intended to be shrunk, such as for example, shoulder tissue of treatment region 70 of FIG. 4. According to one presently preferred embodiment, the tip 62 of the electrosurgical probe is placed against one of the location points 80–109, such as location point 80, and a button, such as switch 66 of FIG. 2, is manipulated so as to cause the electrosurgical probe to emit a stimulation signal to shoulder tissue at location point 80. According to this embodiment, the stimulation signal is applied in a short burst or repeated short bursts so as to keep the shoulder tissue from being directly heated by the RF energy that produces the stimulation signal.

While applying the stimulation signal, observation is made as to whether the axillary nerve is stimulated, step 520. The axillary nerve is stimulated whenever the axillary nerve is located within a nerve stimulation zone, which is the area surrounding the tip 62 within which the stimulation signal is strong enough to stimulate a nerve. Stimulation of the axillary nerve causes contraction of the deltoid muscle, which can be visibly observed. Arthroscopically, stimulation can also be visibly observed as a jump or movement of the shoulder tissue within the field of view of the arthroscope.

If the axillary nerve is not stimulated, the tip 62 of the electrosurgical probe is moved to a new location point, step 530, if it is determined that there is another location point to test, step 540. It may be desirable to systematically apply the stimulation signal to each of the location points 80–109 in the order that they are identified in FIG. 4. This generally enables multiple locations points 80–109 to be tested in a continuous sweeping motion. It should be appreciated, however that the stimulation signal can be applied in any particular order, as desired.

According to one embodiment, the distance between location points 80–109 is within the range of approximately 1 mm to approximately 10 mm, with a preferred distance of approximately 5 mm. It will be appreciated, however, that the distance between location points may vary according to a surgeon's preference and according to general assumptions as to where the axillary nerve may be located. For example, the spacing between location points 80–109 may decrease when prospecting near an area where the surgeon believes the axillary nerve may be located.

When the axillary nerve is stimulated by the stimulation signal then the location point where the stimulation signal is emitted is identified as a high-risk region that is within such close proximity to the axillary nerve that it should be avoided during the thermal shrinking of the surrounding tissue, step 550. According to one example, the axillary nerve is stimulated when the stimulation signal is emitted at location points 94 and 100 of FIG. 4. According to this example, location points 94 and 100 comprise high-risk regions that should be avoided while performing thermal capsullorhaphy to the treatment region 70.

According to one embodiment, high-risk regions that should be avoided during thermal capsullorhaphy also include an area of approximately one square centimeter immediately around any location point where the stimulation signal stimulates the axillary nerve. For example, in FIG. 4, the high-risk region 200 comprises an area of approximately one square centimeter around each of location points 94 and 100, and is generally bounded by location points 88, 90, 102, 101, 106, 108, 96, and 95. The tip 62 of the electrosurgical probe is moved to new location points of the treatment region, step 530, until it is determined that there are no more location points to test, step 540.

Once all the high-risk regions of the treatment region are identified, it is possible to "paint" the remaining shoulder tissue with RF energy in a manner that is required to thermally shrink the shoulder tissue, step 560. This can be accomplished, for example, by pressing a button on the electrosurgical probe that causes RF energy to be continuously dispensed from the tip of the probe while making a sweeping motion with the tip of the probe across the shoulder tissue of the treatment region, while avoiding the high-risk regions.

It should be appreciated that the steps shown in FIG. 5 do not necessarily have to be performed in any particular order, other than step 560 should be performed as the final step. For example, if the stimulation signal is dispensed from the electrosurgical probe in repeating short bursts, while in the nerve stimulation mode, then steps 510, 520, 530, 540, and 550 can be performed simultaneously while moving the tip of the electrosurgical probe across the shoulder tissue in a single continuous sweeping motion.

Figure 6:
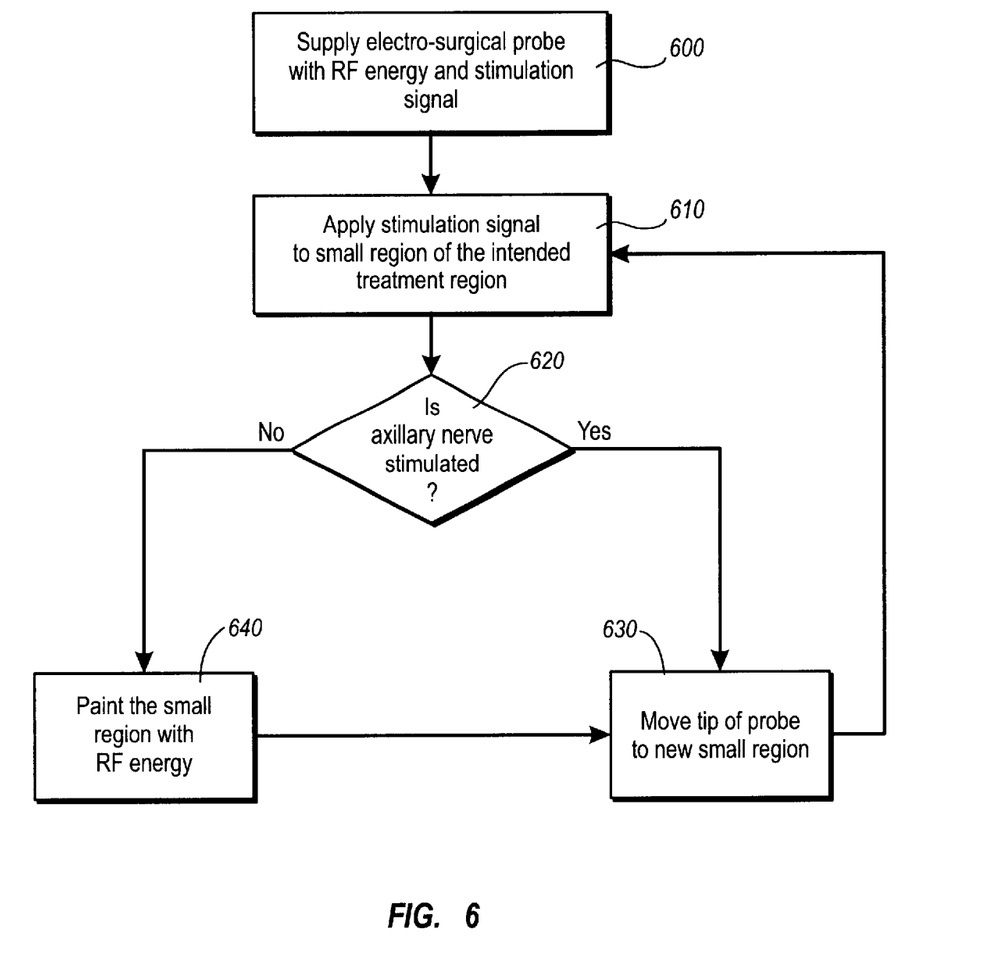
FIG. 6 is a flow diagram that illustrates one alternative embodiment of the methods of the present invention for protecting the axillary nerve while performing thermal capsullorhaphy.

According to another embodiment, a method for protecting the axillary nerve from thermal injury during thermal capsullorhaphy comprises the performance of steps 600–640 of the flowchart illustrated in FIG. 6.

Step 600 involves supplying the electrosurgical probe with RF energy and a stimulation signal. Next, in step 610, the stimulation signal is applied to a small region of the intended treatment region. The term "a small region" is generally defined herein to include any portion of any size of the intended treatment region, and is determined by the preference of the surgeon performing the procedure. For example, with reference to FIG. 4, the small region may comprise any combination or series of proximate location points 80–109. In one embodiment, the small region comprises the row of location points 80–85. In another embodiment, the small region comprises the column of location points 80, 91, 92, 103, and 104. In yet another embodiment, the small region comprises the block of location points 80, 81, 90, and 91.

Step 610 requires the stimulation signal to be applied to the entire small region of the intended treatment region. This may be accomplished in two different ways. First, the stimulation signal can be applied separately and discretely at each of the location points within the small region. Alternatively, the tip of the electrosurgical probe can be moved in a continuous sweeping motion across the entire small region, while emitting the stimulation signal, and thereby effectively applying the stimulation signal to each of the location points within the small region.

While applying the stimulation signal, observation is made as to whether the axillary nerve is stimulated, step 620, which as described above can be visibly observed as a jump or movement of the shoulder tissue within the field of view of the arthroscope. If the axillary nerve is stimulated then the tip of the electrosurgical probe is moved to a new small region, step 630, where the stimulation signal is applied, step 610.

If a small region has been tested and the axillary nerve is not stimulated while testing the small region then the small region is "painted" with RF energy in a manner that is required to thermally shrink the shoulder tissue within the small region, step 640. This can be accomplished, by pressing a button on the electrosurgical probe that causes RF energy to be continuously dispensed from the tip of the probe while making a sweeping motion with the tip of the probe across the small region. The tip of the probe is then moved to a new small region of the intended treatment region, if any remain, where the stimulation signal is applied, steps 630 and 610.

It will be appreciated that the specific examples that have been provided regarding the electrosurgical probe, the electrosurgical generator, and the methods for using the electrosurgical probe and electrosurgical generator to protect the axillary nerve during thermal capsullorhaphy are merely illustrative and should not be construed as limiting the scope of the invention. Accordingly, the devices and methods of the specific embodiments may be modified without departing from the scope of the invention.

For example, in other embodiments, the invention may be practiced in open surgery thermal capsullorhaphy procedures, in which case the electrosurgical probe need not be an arthroscopic probe. The devices and methods of the invention can also be used to identify other nerves than the axillary nerve at different locations on the human body and on different species of animals.

It should also be appreciated that the present invention is not limited to any particular type of nerve stimulation signal. The invention may be practiced with the use of any RF waveform that produces a nerve stimulation signal that is adequate to stimulate a nerve. For example, the electrosurgical generator of the invention can be modified by an electrical circuit to create a stimulation signal that comprises a DC offset signal, which is sufficient to stimulate the axillary nerve, and which is superimposed on existing waveforms. As another alternative, a piezoelectric crystal can be used to create a pulse suitable for nerve stimulation.

What should be understood by the application is that the invention generally provides systems for protecting the axillary nerve from thermal damage during thermal capsullorhaphy. The invention also provides methods for accomplishing this while using standard electrosurgical generators instead of requiring the services of dedicated thermal capsullorhaphy generators. It should be appreciated that these benefits of the invention are advantages over the prior art.

It should also be appreciated that the present invention may be embodied in other forms without departing from its spirit or essential characteristics. As properly understood, the preceding description of specific embodiments is illustrative only and in no way restrictive. The scope of the invention is, therefore, indicated by the appended claims as follows.

What is claimed and desired to be secured by United States Letters Patent is:

1. A surgical device for use in thermally shrinking tissue during an endoscopic procedure while protecting proximate nerves, comprising:

an electrosurgical probe suitable for use in thermally shrinking tissue through the emission of radiofrequency energy;

connection means for electronically connecting said probe to a radiofrequency energy generator;

first switching means for selectively causing said probe to emit a quantity of radiofrequency energy that at least indirectly results in stimulation of a nerve in the vicinity of the probe when used in a saline environment but that is insufficient to cause irreversible thermal injury to the nerve; and second switching means for selectively causing said probe to emit a quantity of radiofrequency energy sufficient to thermally shrink tissue.

2. A surgical device as defined in claim 1, wherein the surgical device is connected to a radiofrequency energy generator that is capable of producing radiofrequency energy having a coag waveform.

3. A surgical device as defined in claim 1, wherein the electrosurgical probe includes a conductive tip encased within an insulating body.

4. A surgical device as defined in claim 3, wherein said first switching means comprises a first electronic switch disposed at least partially within said insulating body.

5. A surgical device as defined in claim 4, wherein said first electronic switch causes said probe to emit radiofrequency energy from said tip for a duration of less than about 0.5 second.

6. A surgical device as defined in claim 4, wherein said second switching means comprises a second electronic switch disposed at least partially within said insulating body.

7. A surgical device as defined in claim 6, wherein said second electronic switch causes said probe to continuously emit radiofrequency energy from said tip.

8. A surgical device as defined in claim 1, wherein the electrosurgical probe emits radiofrequency energy through one of either a monopolar electrode and a bipolar electrode.

9. A surgical device as defined in claim 1, wherein the electrosurgical probe emits a nerve stimulation pulse by means of a piezoelectric crystal.

10. A surgical device as defined in claim 1, wherein the surgical device is specifically adapted for use in shrinking ligaments near an axillary nerve in a human shoulder while avoiding irreversible thermal damage to the axillary nerve.

11. A surgical device for use in thermally shrinking tissue during an endoscopic procedure while protecting proximate nerves, comprising:

an electrosurgical probe suitable for use in selectively stimulating a nerve and thermally shrinking tissue by emission of radiofrequency energy from a tip of said probe when used in a saline environment; and at least one connection used to electronically connect said probe to a radiofrequency energy generator;

said electrosurgical probe being able to selectively operate in a nerve stimulation mode in which the tip of the probe emits radiofrequency energy in a manner so as to stimulate, but not irreversibly thermally damage, a nerve within a nerve stimulating zone adjacent said tip and in a tissue shrinkage mode in which the tip of the probe emits radiofrequency energy in a manner so as to thermally shrink tissue within a tissue shrinkage zone adjacent said tip.

12. A surgical device as defined in claim 11, wherein said electrosurgical probe includes a switch that, when activated, selectively causes said tip of said probe to emit a quantity of radiofrequency energy for a duration of less than about 0.5 second in order to stimulate but not damage any nerves in the nerve stimulation zone.

13. A surgical device as defined in claim 12, wherein said quantity of radiofrequency energy comprises a coag waveform.

14. A surgical device as defined in claim 11, wherein said electrosurgical probe includes a switch that, when activated, selectively causes said tip of said probe to continuously emit a quantity of radiofrequency energy in order to thermally shrink tissue in the tissue shrinkage zone.

15. A surgical device as defined in claim 14, wherein said quantity of radiofrequency energy has at least one of a coag or cut waveform.

16. A surgical device as defined in claim 11, further comprising means for indicating when the electrosurgical probe is operating in the nerve stimulation mode and when the electrosurgical probe is operating in the thermal shrinkage mode.

17. A surgical device as defined in claim 11, wherein the surgical device is specifically adapted for use in shrinking ligaments near an axillary nerve in a human shoulder while avoiding irreversible thermal damage to the axillary nerve.

18. A system used in thermally shrinking tissue during an endoscopic procedure while protecting proximate nerves, comprising:
   an electrosurgical probe suitable for use in selectively stimulating a nerve and thermally shrinking tissue through the emission of radiofrequency energy from a tip of said probe when used in a saline environment;
   a radiofrequency energy generator that generates radiofrequency energy in a manner that allows said electrosurgical probe to selectively stimulate a nerve using radiofrequency energy and thermally shrink tissue using radiofrequency energy;
   connection means for electronically connecting said probe to said generator;
   first switching means associated with said probe for selectively causing said probe to emit a quantity of radiofrequency energy that at least indirectly results in stimulation of a nerve within a nerve stimulation zone adjacent said tip of said probe without irreversibly injuring said nerve; and
   second switching means associated with said probe for selectively causing said probe to emit a quantity of radiofrequency energy sufficient to thermally shrink tissue within a tissue shrinkage zone adjacent said tip of said probe.

19. A system as defined in claim 18, wherein said generator is capable of generating radiofrequency energy having a coag wave form at a power suitable for use in stimulating a nerve in a saline environment when said first switching means is activated.

20. A system as defined in claim 18, wherein said generator is capable of generating radiofrequency energy having at least one of a coag or a cut wave form at a power suitable for use in thermally shrinking tissue when said second switching means is activated.

21. A system as defined in claim 18, wherein the electrosurgical probe is specifically adapted for use in shrinking ligaments near an axillary nerve in a human shoulder while avoiding irreversible thermal damage to the axillary nerve.

22. A method for thermally shrinking tissue while protecting nerves associated with said tissue, comprising:
   providing an electrosurgical probe capable of selectively emitting radiofrequency energy from a tip of said probe in a first manner so as to stimulate a nerve within a nerve stimulation zone adjacent said tip and in a second manner so as to thermally shrink tissue within a tissue shrinkage zone adjacent said tip;
   defining a treatment region of shrinkable tissue within a mammal to be treated by said electrosurgical probe;
   step for locating at least one nerve within or near said treatment region; and
   step for thermally shrinking at least a portion of said shrinkable tissue within said treatment region while avoiding irreversible thermal damage to said at least one nerve within or near said treatment region.

23. A method as defined in claim 22, wherein said nerve locating step includes emitting a quantity of radiofrequency energy having a coag wave form from said tip in manner so as to result in stimulation of a nerve within said nerve stimulation zone and maintain said nerve stimulation zone at a temperature sufficiently low so as to avoid permanent thermal damage to said nerve.

24. A method as defined in claim 22, wherein said tissue shrinking step includes emitting a quantity of radiofrequency energy having at least one of a coag or cut wave form from said tip in a manner so as to heat said tissue shrinkage zone to a temperature sufficient to thermally shrink tissue.

25. A method as defined in claim 22, wherein said method involves shrinking ligaments near an axillary nerve in a human shoulder while avoiding irreversible thermal damage to the axillary nerve.

* * * * *

UNITED STATES PATENT AND TRADEMARK OFFICE
CERTIFICATE OF CORRECTION

PATENT NO. : 6,618,626 B2
DATED : September 9, 2003
INVENTOR(S) : Hugh S. West, Jr. and John S. Gentelia It is certified that error appears in the above-identified patent and that said Letters Patent is hereby corrected as shown below:

<u>Title page,</u>
Item [56], U.S. PATENT DOCUMENTS, after "Aaron" insert -- F. --

<u>Column 3,</u>
Line 29, after "nerve" insert -- . --

<u>Column 8,</u>
Line 23, after "mode" start a new paragraph

Signed and Sealed this

Sixteenth Day of March, 2004

JON W. DUDAS
*Acting Director of the United States Patent and Trademark Office*